US006783507B1

(12) United States Patent
Fisher

(10) Patent No.: US 6,783,507 B1
(45) Date of Patent: Aug. 31, 2004

(54) THUMB SPLINT

(76) Inventor: Harold Fisher, 540 Briar Hill Avenue, Toronto, Ontario (CA), M5N 1M9

( * ) Notice: Subject to any disclaimer, the term of this patent is extended or adjusted under 35 U.S.C. 154(b) by 0 days.

(21) Appl. No.: 09/869,849

(22) PCT Filed: Nov. 6, 2000

(86) PCT No.: PCT/CA00/01292

§ 371 (c)(1),
(2), (4) Date: Oct. 18, 2001

(87) PCT Pub. No.: WO01/34070

PCT Pub. Date: May 17, 2001

(30) Foreign Application Priority Data

Nov. 8, 1999 (CA) .............................................. 2286959

(51) Int. Cl.[7] .................................................. A61F 5/00
(52) U.S. Cl. ................................. 602/22; 602/5; 602/21
(58) Field of Search ................................. 602/5, 20–22, 602/62, 64, 60, 61, 75, 76, 77, 78, 79, 41, 42; 128/878–880, 876; 473/450, 458, 615; 482/47, 48; 2/163

(56) References Cited

U.S. PATENT DOCUMENTS

| | | | | |
|---|---|---|---|---|
| 3,533,405 A | * | 10/1970 | Collins | ........................ 482/48 |
| 3,707,730 A | * | 1/1973 | Slider | .......................... 2/161.1 |
| 3,888,482 A | * | 6/1975 | Starrett et al. | ............... 473/458 |
| 4,369,775 A | | 1/1983 | Gamm | |
| 4,632,105 A | | 12/1986 | Barlow | |
| 4,638,764 A | * | 1/1987 | Anderson | .................... 119/770 |
| 4,706,658 A | * | 11/1987 | Cronin | ................ 128/DIG. 20 |
| 4,709,694 A | | 12/1987 | O'Connell | |
| 4,953,568 A | * | 9/1990 | Theisler | ....................... 128/878 |
| 5,188,356 A | | 2/1993 | Furr et al. | |
| 5,787,896 A | * | 8/1998 | Sackett | ........................ 128/880 |
| 5,916,187 A | * | 6/1999 | Brill | ............................ 602/21 |

FOREIGN PATENT DOCUMENTS

AT 401868 12/1996

* cited by examiner

Primary Examiner—Michael A. Brown
Assistant Examiner—Fenn C. Mathew
(74) Attorney, Agent, or Firm—Greer, Burns & Crain, Ltd.

(57) ABSTRACT

A thumb splint comprises a thumb receiving section for receiving a thumb of a user, an index finger receiving section for receiving an index finger of a user, a non-extendable, flexible connector extending between and secured to the thumb receiving section and the index finger receiving section for limiting abduction of the thumb to a predetermined value while permitting the thumb and index finger to move in a pinching action; and an elongated strap secured to the index finger receiving section for keeping the thumb and index finger receiving sections operatively positioned on the index finger and thumb, respectively.

2 Claims, 3 Drawing Sheets

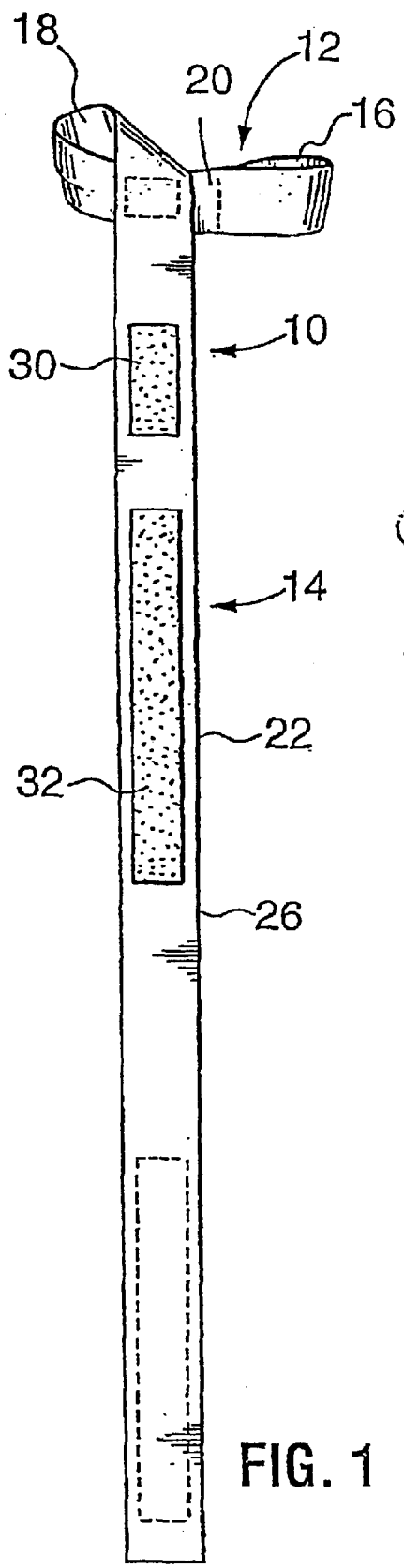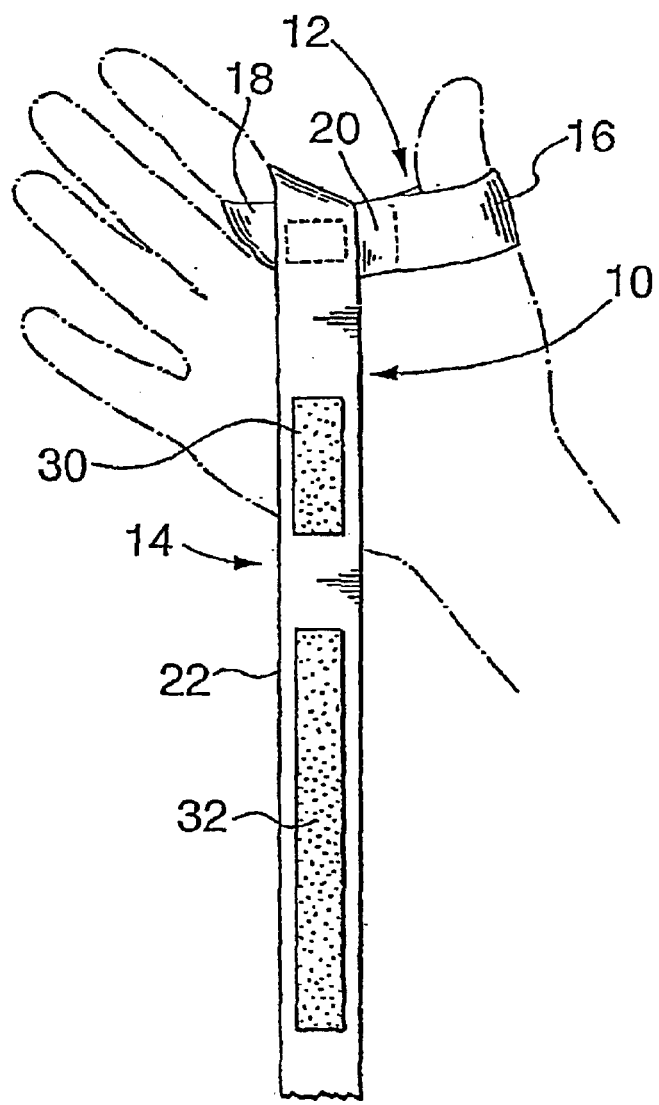
FIG. 1
FIG. 2

THUMB SPLINT

The present invention relates to a thumb splint for use in protecting and preventing injury to an injured or uninjured ulnar collateral ligament at the base of the thumb.

BACKGROUND OF THE INVENTION

A sprain is a joint injury that causes a stretch or tear in a ligament, which is a strong band of tissue which connects one bone to another. A sprain of the ulnar collateral ligament in the thumb is a common injury in skiing and commonly referred to as "Skier's Thumb". It may occur when one falls onto an outstretched thumb, bending the thumb back toward the arm. This stretches and injures the ulnar collateral ligament. It may also be caused by a skier catching a thumb on a ski pole strap. The sprain may occur in other activities when one falls onto an outstretched thumb or when a thumb gets hooked onto another player's jersey or face mask. The injury results in pain, swelling, and tenderness at the inner part of the base of your thumb where the thumb attaches to the hand. The patient may find it difficult to hold an object in his hand and apply force with the thumb. Moving the thumb causes pain.

Treatment varies with the severity of the injury. Grade III sprain with a very loose joint requires surgery to repair the ligament. Grade I and II sprains may be treated with a cast, taping, or splinting so that the thumb does not move for up to six weeks.

The drawback of taping the thumb is that a relatively large amount of tape is required, the tape is relatively heavy and cumbersome and must be replaced relatively frequently, usually with assistance from another person.

Hand splint devices commonly used for the thumb typically utilize a rigid splint which secure the thumb in a fixed position by supporting the back side of the thumb and prevents any flexing of the thumb. Such rigid and fixed methods of support effectively completely immobilize the thumb. However, it is desirable to support the thumb in a manner which permits normal movement of the hand and full motion of the thumb, but prevents the hyper-extension of the thumb backwards. Prior art devices generally do not permit such full motion of the thumb. Further, prior art supports and splints generally obstruct the palm of the hand and thus render the hand movement substantially debilitated. Prior art also may require a glove or glove system to be worn rather than a simple unobtrusive fabric.

SUMMARY OF THE INVENTION

The present invention seeks to provide a thumb splint which protects the thumb while allowing substantially normal motion of the hand and thumb without rigid components or necessity to be used as part of a glove, and yet which is of low cost, lightweight, comfortable, easy to apply or remove, and easy to manufacture since it is made of one continuous ribbon of material folded and sewn/bonded.

The present invention is generally defined as a thumb splint comprising a thumb stabilizing component for securing the thumb of the user to the adjacent index finger permitting the thumb to move toward the index finger and leaving the digits free but limiting movement of the thumb away from the index finger to a predetermined angle; and a positioning component for securing the thumb stabilizing component in proper position on the hand of the user.

This unobtrusive and lightweight design will allow it to be used without a glove (e.g. basketball, tennis), or to fit under any other sports glove (e.g. skiing, hockey, baseball, etc.).

BRIEF DESCRIPTION OF THE DRAWINGS

These and other features of the invention will become more apparent from the following description in which reference is made to the appended drawings in which:

FIG. 1 is a plan view of a thumb splint in accordance with one embodiment of the present invention;

FIG. 2 is a plan view of a thumb splint illustrating the thumb stabilizing portion of the splint operatively positioned on the hand of a user;

FIGS. 2, 3 and 4 are a plan views illustrating the various stages of the procedure of applying the positioning component of the splint is applied.

DETAILED DESCRIPTION OF PREFERRED EMBODIMENT OF THE INVENTION

Figure 3:
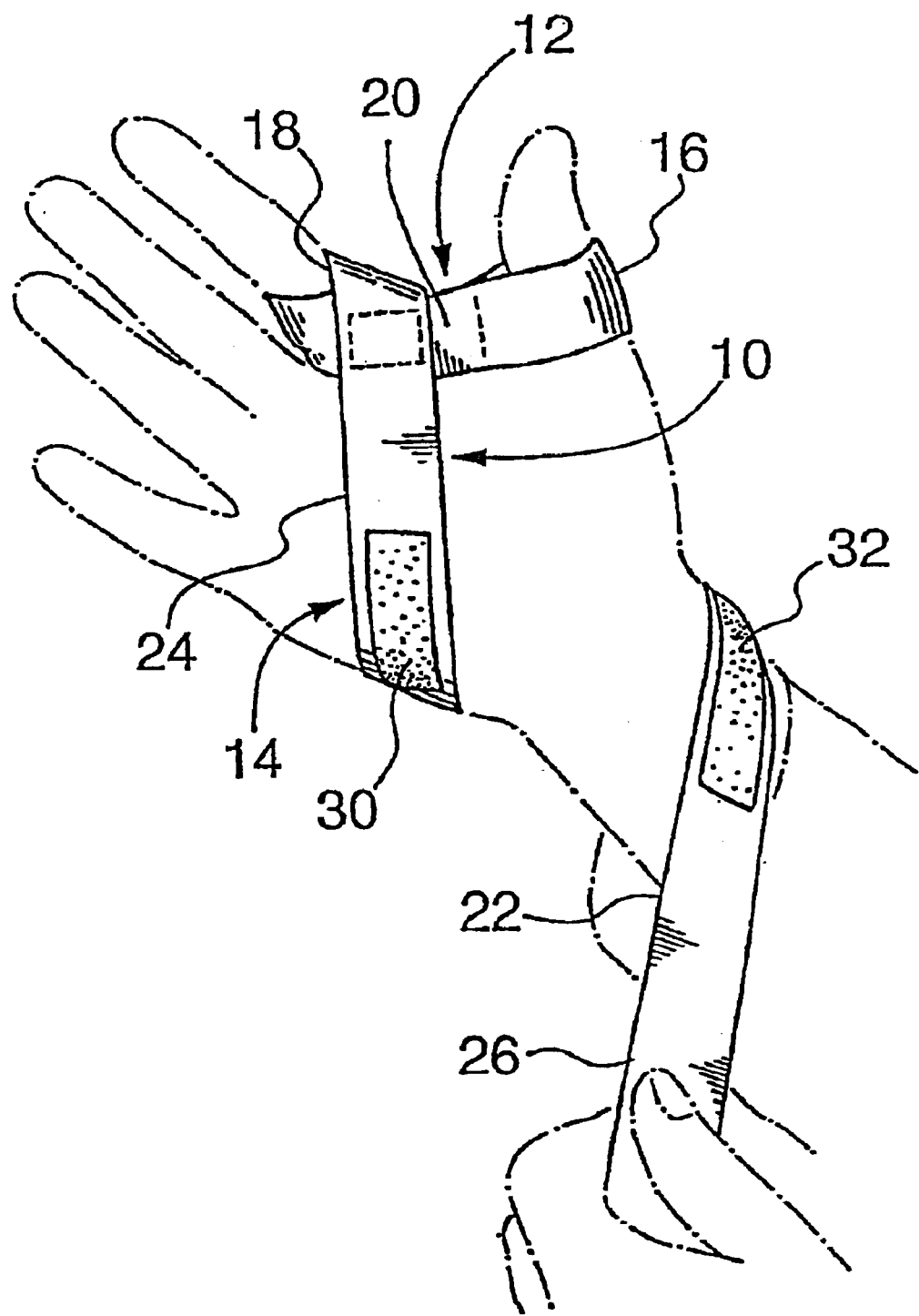

FIG. 1 illustrates an embodiment of a thumb splint 10 of the present invention. The splint is generally comprised of a thumb stabilizing component 12 and a positioning component 14 for keeping the stabilizing component in proper position on the wearer's hand.

The stabilizing component 12 permits the thumb and index finger to move towards one another but precludes them from moving apart (abduct) beyond a predetermined angle. As best shown in FIG. 2, the stabilizing component comprises a thumb receiving section 18, an index finger receiving section 16 and a flexible, non-extendable, connector 20 which extends between and is secured to the thumb and finger receiving sections. The thumb receiving section 16 is arranged to engage a substantial portion of the side of the proximal phalanx bone of the thumb remote from the index finger. The index finger receiving section receives the index finger of the wearer and is positioned proximate the joint at which the index finger is connected to the hand; the carpometacarpal joint. The connector is flexible so as to permit the thumb and index finger to move towards one another in a pinching action, allowing the wearer to grip a ski pole or the like, and of a length which limits the thumb to move to a maximum angular distance with respect to the index finger in the order of about 90 to 100 degrees.

Both sections are formed to minimize the stresses applied to the thumb and index finger. This is achieved by forming the sections from relatively thin, wide straps which provide a relatively large skin engaging surface area. The connector may be made of any suitable material capable of absorbing forces applied to the thumb and index finger. Thus, the connector may be integral with the thumb and index finger receiving sections. Alternatively, the connector could be a separate element in the form of a narrow strip of material or a string or wire of suitable strength. In one embodiment of the invention, both sections and the connector are formed of thin, light weight material such as polyester or nylon webbing having a width of about 2.5 cm.

The positioning component serves to keep the thumb stabilizing component in proper position by drawing the stabilizing component toward the wrist of the wearer. In accordance with a preferred embodiment of the invention, the positioning component is comprised of an elongated strap 22. One end 24 of the strap is secured to the stabilizing component proximate the index finger receiving section. The other end 26 of the strap is releasably connectable to the stabilizing component or to the one end 24 of the strap. A preferred releasable connector comprises a pair of inter-engageable velcro strips 30 and 32. One of the velcro strips is secured to the one end 24 of the strap and the other strip is secured to the other end 26 of the strap. It will be understood that various other releasable connectors may be employed, including buttons, snaps, and the like.

The strap is of sufficient length so as to extend from the stabilizing component, along the palm of the hand, wrap around the wrist once, and then extend along the back side of the hand and releasably engage either the stabilizing component or the first end of strap. Preferably, the strap applies substantially equal forces to both sides the thumb and finger receiving sections so that both are kept firmly in position.

In a preferred embodiment of the invention, the splint is formed of a single strip of webbing material of uniform width of about 2.5 cm. The thumb receiving section is formed by folding one end of the strip onto itself and securing it to the strip by sewing. The index finger receiving section is formed a suitable distance from the thumb receiving section by again folding over the end of the strip such that the length of the web extends substantially transversely of the length of the webbing material and secured there by sewing. The portion of the web between the thumb and index finger receiving sections constitutes the connector. The balance of the length of webbing is the positioning strap.

Figure 4:
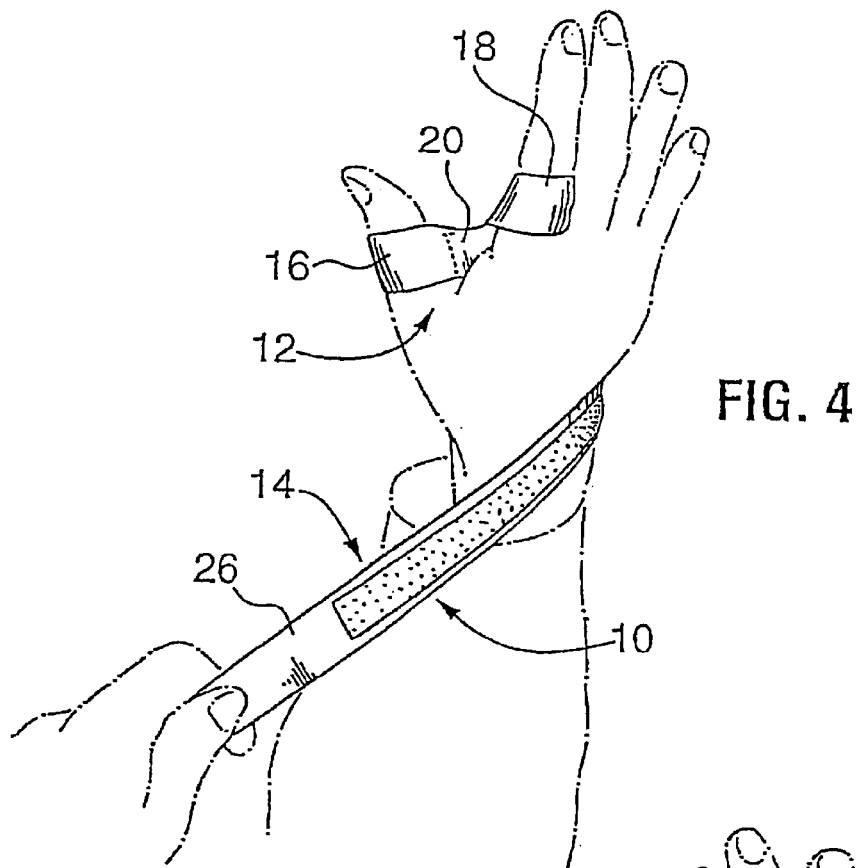
Figure 5:
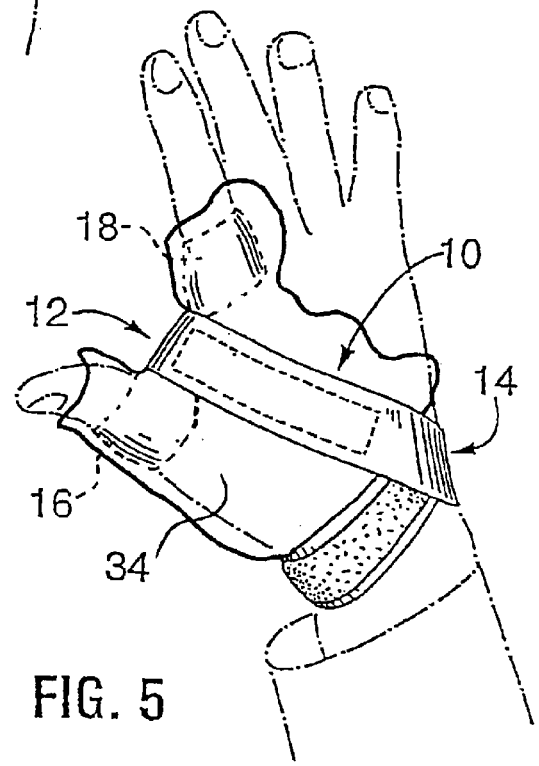
FIG. 5 is a plan view of the back of the hand of a user showing the splint in its normal applied position.

To apply the splint, the user simply inserts his or her thumb and index finger into the thumb and index finger receiving sections, respectively, as shown in FIG. 2. The index finger receiving section is fitted snugly against the metacarpophalangeal joint. The thumb receiving section is positioned so that its width extends along the side of the proximal phalanx remote from the index finger. The strap is then drawn downwardly toward the wrist over the palm of the hand, pulled around the back of the hand and wrist as shown in FIG. 3, and then around the front of the wrist, and then pulled upwardly along the backside of the hand (FIG. 4), between the thumb and index finger and secured by engaging the two velcro strips 30 and 32. The final applied configuration is shown in FIG. 5.

The splint could be used alone or incorporated into the production of various types of gloves so that it would be in place when a skier pulls the gloves on. Referring to FIG. 5, a glove 34 is shown fragmentarily, showing the splint 10 incorporated therein. While primarily designed for skiing, the thumb splint would also be appealing in other sports and activities where an unsupported thumb can be damaged easily.

It will be seen that the thumb splint of the present invention fulfills the need for a thin, light weight, splint that would prevent a skier from injuring his thumbs and that would be of low cost, comfort, and ease of application or removal.

The splint limits the abduction of the thumb to between 90 and 100 degrees, limits the extension of the thumb to between 90 and 100 degrees, and limits the posterior translation of the thumb. This would provide protection in the event of a fall so that the wearer is not injured.

For increased appeal, the thumb splint is light and thin so that it is comfortable to wear. The splint does not interfere with the wearer's ability to move his thumbs or fingers, and can still grip the handles of his ski poles. The straps could be worn by themselves or under a pair of gloves. The straps could also be incorporated into the production of a pair of liner gloves or a pair of waterproof, insulated outer gloves. It will also be seen that the splint is quick and easy to put on or take off, and is readily adjustable for a comfortable fit. The straps would fit snugly, but would not restrict the flow of blood to the fingers or thumbs, and they would not cause the wearer's hands to sweat excessively.

Although the present invention has been described with reference to its preferred embodiments, those skilled in the art will recognize changes which may be made in form or structure which do not depart from the spirit of the invention already described in the specification and embodied in the claims which follow.

What is claimed is:

1. A thumb splint comprising:

a thumb stabilizing component for securing the thumb of the user to the adjacent index finger permitting the thumb to move toward the index finger but limiting movement of the thumb away from the index finger to a predetermined angle, said thumb stabilizing component comprising:

a thumb receiving section for receiving a thumb of a user;

an index finger receiving section for receiving an index finger of a user, a non-extendable, flexible connector extending between and secured to the thumb section and the index finger section for permitting the thumb and index finger to move towards one another, but limiting the movement of the index finger away from the thumb beyond a predetermined value;

a positioning component for securing the thumb stabilizing component in proper position on the hand of the user, said positioning component comprising an elongated strap having a first end secured to said thumb stabilizing component at a point between said thumb receiving section and said index finger receiving section and a second end releasably securable to said first end of said strap or to said stabilizing component for keeping the stabilizing component firmly and operatively positioned on the hand of the user and wherein said splint is incorporated into a glove or mitt; and said strap having a length sufficient to extend from said stabilizing component, along the palm of the hand of the user, to and around the wrist and alone the backside of the hand.

2. A thumb splint as defined in claim 1, said thumb stabilizing component and said positioning component being integral and formed of a single length of polyester or nylon or other suitable fabric webbing.

* * * * *